US010383643B2

(12) United States Patent
LaPrade et al.

(10) Patent No.: US 10,383,643 B2
(45) Date of Patent: Aug. 20, 2019

(54) METHODS AND DEVICES FOR ATTACHING OR REATTACHING SOFT TISSUE TO BONE

(71) Applicant: Smith & Nephew, Inc., Memphis, TN (US)

(72) Inventors: Robert LaPrade, Avon, CO (US); Coen Wijdicks, Munich (DE); Stephen Santangelo, Sturbridge, MA (US)

(73) Assignee: Smith & Nephew, Inc., Memphis, TN (US)

( * ) Notice: Subject to any disclaimer, the term of this patent is extended or adjusted under 35 U.S.C. 154(b) by 216 days.

(21) Appl. No.: 15/303,880

(22) PCT Filed: May 6, 2015

(86) PCT No.: PCT/US2015/029465
§ 371 (c)(1),
(2) Date: Oct. 13, 2016

(87) PCT Pub. No.: WO2015/171761
PCT Pub. Date: Nov. 12, 2015

(65) Prior Publication Data
US 2017/0042556 A1    Feb. 16, 2017

Related U.S. Application Data

(60) Provisional application No. 61/990,329, filed on May 8, 2014.

(51) Int. Cl.
*A61B 17/17*    (2006.01)
*A61B 17/04*    (2006.01)
(Continued)

(52) U.S. Cl.
CPC ...... *A61B 17/1714* (2013.01); *A61B 17/0401* (2013.01); *A61B 17/16* (2013.01);
(Continued)

(58) Field of Classification Search
CPC .......................................... A61B 1/17–17/1796
See application file for complete search history.

(56) References Cited

U.S. PATENT DOCUMENTS 5,324,295 A * 6/1994 Shapiro .............. A61B 17/1714
606/86 R
5,385,567 A    1/1995 Goble
(Continued)

FOREIGN PATENT DOCUMENTS

WO    2006039266    4/2006
WO    2012110783    8/2013

OTHER PUBLICATIONS

International Search Report and Written Opinion dated Aug. 14, 2015, for PCT Application No. PCT/US2015/029465.
(Continued)

*Primary Examiner* — Zade Coley
(74) *Attorney, Agent, or Firm* — Norman F. Hainer, Jr.

(57) ABSTRACT

Embodiments of the invention include implants, instruments, and methods for attaching or reattaching soft tissue (200, 2200) to a bone (100), that enable independent tensioning of multiple connectors such as sutures (60, 160, 2060, 2160) and enable redundant fixation between bone (100) and soft tissue (200, 2200). Some embodiments provide for improved accuracy of the placement of substantially parallel tunnels through which soft tissue (200, 2200) to bone (100) connectors such as sutures (60, 160, 2060, 2160) are passed.

16 Claims, 7 Drawing Sheets

(51) Int. Cl.
*A61F 2/08* (2006.01)
*A61B 17/16* (2006.01)

(52) U.S. Cl.
CPC .... *A61F 2/0805* (2013.01); *A61B 2017/0404* (2013.01); *A61F 2002/0852* (2013.01); *A61F 2002/0882* (2013.01); *A61F 2240/005* (2013.01); *A61F 2250/0097* (2013.01)

(56) References Cited

U.S. PATENT DOCUMENTS

| | | | |
|---|---|---|---|
| 6,030,391 A | 2/2000 | Brainard et al. | |
| 6,613,002 B1 * | 9/2003 | Clark | A61B 5/1076 600/104 |
| 7,572,283 B1 | 8/2009 | Meridew | |
| 9,119,645 B2 * | 9/2015 | McBride | A61B 17/1757 |
| 2004/0260307 A1 * | 12/2004 | Zander | A61B 17/17 606/104 |
| 2008/0086144 A1 * | 4/2008 | Zander | A61B 17/17 606/96 |
| 2013/0177938 A1 | 7/2013 | Ward | |
| 2013/0282016 A1 | 10/2013 | Volpi et al. | |

OTHER PUBLICATIONS

Chinese Application No. 201580037080.0 First Office Action dated Jul. 30, 2018.
European Application No. 15789150.8-1122 Office Action.
Examination Report No. 1 for Australian Patent Application No. 2015256066 dated Feb. 25, 2019.
Japanese Notice of Reasons for Rejection—Application No. 2016-566882 dated Mar. 28, 2019.

* cited by examiner

METHODS AND DEVICES FOR ATTACHING OR REATTACHING SOFT TISSUE TO BONE

FIELD OF THE INVENTION

The present invention relates generally to the field of surgical methods and medical devices, and more particularly relates to methods and devices for attaching or reattaching soft tissue to bone. Some embodiments include specific methods and devices for reattaching a detached medial meniscus posterior root to a tibia. Some embodiments include specific methods and devices for reattaching a torn radial meniscus to a tibia.

BACKGROUND

Anatomically correct attachment of soft tissue to bone is essential to the healthy and effective operation of many musculoskeletal joints and systems. By way of illustrative example, medial meniscus posterior root attachment is essential in providing evenly distributed hoop stresses in meniscal cartilage and thereby enabling healthy load-sharing across a knee. As such, a detachment of a medial meniscus at its posterior root or a radial tear in the meniscus may damage circumferential integrity of a meniscus and lead to rapid progression of arthritis. A medial posterior root repair radial tear repair, therefore, may be useful to improve medial compartment load distribution and help restore joint mechanics. Medial meniscus repair that includes routing of repair devices such as sutures through a trans-tibial channel is known in the prior art. However, prior art disclosures do not provide for sufficiently effective methods and devices to reattach a meniscus or other soft tissue in a controlled and reproducible manner. Many prior art repair methods, for example, only provide for attaching a meniscus with a single suture, for attaching a meniscus from a single orientation, or for attaching a meniscus with multiple sutures that are dependent on one another such that failure of one suture would lead to the failure or ineffectiveness of another suture.

It would be advantageous to provide methods and devices of repair that use multiple repair devices such as sutures to independently apply tension to the meniscus at multiple locations. Some improved methods and devices may control the meniscus relative to the tibia to which the meniscus is to be reattached by separately tensioning repair devices such as sutures attached to the meniscus at multiple locations. Where multiple attachment locations are oriented to provide for opposing or partially opposing orientations of attachment, independent tensioning of repair devices such as sutures of improved systems may provide for selectable positioning of the reattached meniscus relative to a tibia. Improved methods and devices may also provide for attachments of repair devices with repair devices that are independent of one another such that a failure of one repair device would not contribute to the failure of another repair device. Some improved methods and devices may provide for creation of multiple channels through which one or more dependent or independent repair devices may be passed when attached to a meniscus to be repaired.

SUMMARY

An embodiment of the invention is a method of reattaching soft tissue to a bone. Method embodiments may include creating a first tunnel through the bone such that an exit of the first tunnel is near a first portion of the soft tissue to be reattached. Method embodiments may further include placing a first instrument through the first tunnel that includes a distal mark near its distal end to designate a radial position of the first instrument and a proximal mark near its proximal end that correlates with the distal mark, observing a radial position of the distal mark on the first instrument, and orienting the first instrument such that the distal mark indicates a desired radial position to a second tunnel to be created through the bone such that an exit of the second tunnel is near a second portion of the soft tissue to be reattached. Embodiments of the method may also include observing a radial position of the proximal mark that correlates with the oriented distal mark and creating the second tunnel relative to the first tunnel at a radial direction from the first tunnel indicated by the proximal mark. Method embodiments may further include coupling a first suture to the first portion of the soft tissue to be reattached and passing the first suture through at least one of the first tunnel and the second tunnel, coupling a second suture to the second portion of the soft tissue to be reattached and passing the second suture through at least one of the first tunnel and the second tunnel, tensioning the first suture to bring the soft tissue into contact with the bone, securing the first suture relative to the bone, tensioning the second suture to bring the soft tissue into contact with the bone, and securing the second suture relative to the bone.

Another embodiment of the invention is a method of placing two substantially parallel tunnels in a bone with a controlled distance and relative radial position between the two tunnels. Embodiments of the method may include creating a first tunnel in the bone, placing a first instrument through the first tunnel, wherein the first instrument includes a distal mark near its distal end to designate a radial position of the first instrument and a proximal mark near its proximal end that correlates with the distal mark, observing a radial position of the distal mark on the first instrument and orienting the first instrument such that the distal mark indicates a desired radial position to a second tunnel to be created in the bone, measuring a distance from the exit of the first tunnel to a desired location of the second tunnel, observing a radial position of the proximal mark that correlates with the oriented distal mark, and creating the second tunnel relative to the first tunnel at a radial direction indicated by the proximal mark.

Yet another embodiment of the invention is an instrument set for creating two substantially parallel tunnels in a bone with a controlled distance and relative radial position between the two tunnels. Embodiments of the instrument set may include a first instrument configured to create or maintain a first tunnel through the bone, a drill guide with two or more radial indicia extending from a central hole, the radial indicia being configured to be aligned with the proximal mark to provide a radial direction for the creation of a second tunnel that is substantially parallel with the first tunnel, wherein two or more of the radial indicia include along their respective lengths a respective guide hole at a predetermined distance from the central hole. Embodiments of an instrument set may also include a second instrument configured to be passed through at least one of the guide holes to create a second tunnel that is substantially parallel with the first tunnel. Embodiments of the first instrument may include a shaft with a proximal end and a distal end, a distal mark near the distal end of the shaft configured to designate a radial position of the first instrument, and a proximal mark near the proximal end of the shaft that correlates with the radial position of the distal mark.

DETAILED DESCRIPTION

Figure 1:
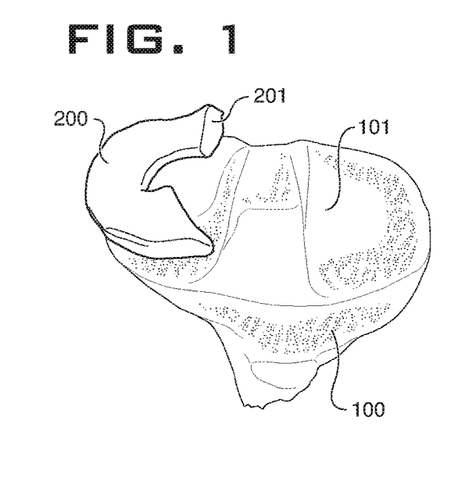
FIG. 1 is a perspective view of a tibial plateau and a portion of a medial meniscus.

A bone and a portion of soft tissue are illustrated in FIG. 1. In particular, a tibia 100 with a tibial plateau 101 is shown with a portion of a medial meniscus 200. In FIG. 1, a posterior root 201 of the medial meniscus 200 that has been partially resected is separated from the tibial plateau 101, and consequently is in need of repair by reattachment. Methods and devices described herein are illustrated in association with reattachment of a posterior root of a medial meniscus and a radially torn medial meniscus; however, the methods and devices described may be equally applicable to other repairs involving attaching or reattaching of soft tissue to bone. Reattachment or repair may be accomplished, for example and without limitation, on a lateral meniscus or any other soft tissue structure. The soft tissue attached or reattached may be cartilage, ligaments, tendons, or any combination or part of these soft tissues or others. The bone to which soft tissue is reattached may be, for example and without limitation, a tibia, femur, patella, humerus, radius, or any combination or part of these bones or others. Soft tissue attached, reattached, repaired, or brought into contact with bone in various embodiments may consequently be given the opportunity to grow into the bone. Reference will be made to FIGS. 2-21 and 23-25 to describe method embodiments of the invention, as well as instruments and implants that may be employed to carry out various method embodiments.

Figure 2:
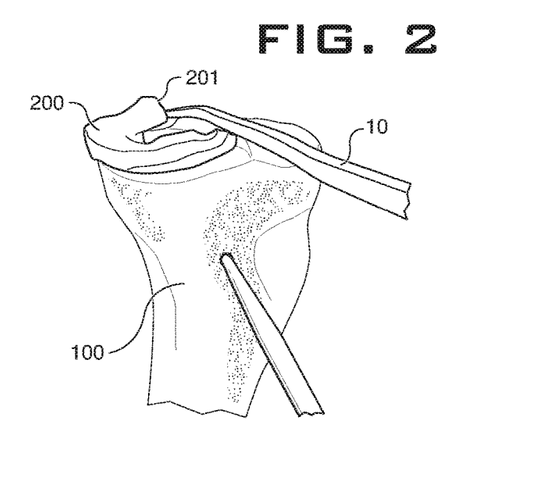
FIG. 2 is a perspective view of an aiming guide or aimer in position on a tibia.
Figure 3:
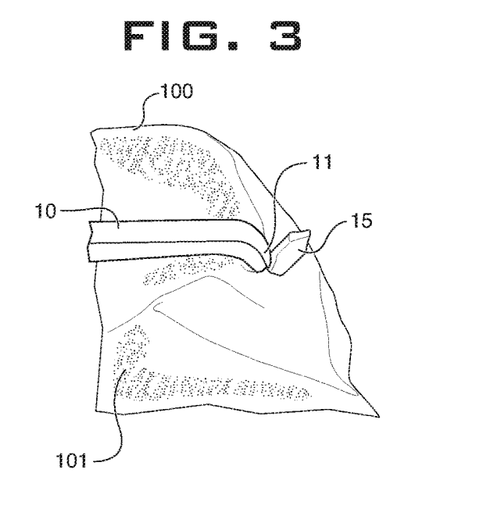
FIG. 3 is a perspective view of the aimer and tibia of FIG. 2 following creation of a first tunnel through the tibia with a first drill.

Method embodiments include creating a first tunnel through a bone, such as a tibia, such that an exit of the first tunnel is near a first portion of soft tissue to be reattached. As shown in FIG. 2, an aimer 10 is used to point to an exit through the tibial plateau 101 near a first portion of the posterior root 201 of the medial meniscus 200 to be reattached. The aimer 10 and other instruments and implants of the methods disclosed herein may be used in combination with endoscopic visualization and manipulation tools. As illustrated in FIG. 3, a drill bit 15 is depicted exiting the tibial plateau 101 slightly distal to the aimer point 11. A drill bit such as the drill bit 15, may be used independently or in conjunction with another instrument to create a tunnel. For example, a drill bit may be used in combination with a sleeved drill such as the sleeved drill 1 illustrated in FIG. 4. By way of further example, the sleeved drill 1 and the drill bit 15 may be used simultaneously by inserting the drill bit 15 inside of the sleeved drill 1 during use or sequentially by first boring a hole with the drill bit 15 followed by passing the sleeved drill 1 through the hole created by the drill bit 15. Non-limiting examples of drill mechanisms in addition to bits include augers, stylets, corkscrews, or any other effective drilling mechanism. Any other instrument or combination of instruments that may be used to effectively create a tunnel through a bone may be used in various embodiments. The sleeved drill 1 is a tubular shaft that includes teeth and a distal mark 2 near its distal end that designates a radial position of the sleeved drill 1 by providing a line longitudinally along the sleeved drill 1 at one radial position. The sleeved drill 1 also includes (FIG. 5) a proximal mark 3 near its proximal end that correlates with the radial position of the distal mark 2. In this example, the proximal mark 3 is also a line marked longitudinally along the sleeved drill 1 at one radial position. In the illustrated embodiment, the distal mark 2 and the proximal mark 3 are part of the same line marked longitudinally along the sleeved drill 1; however, in other embodiments a distal mark and a proximal mark may have some correlation that does not necessarily include coexisting along the same line.

Figure 4:
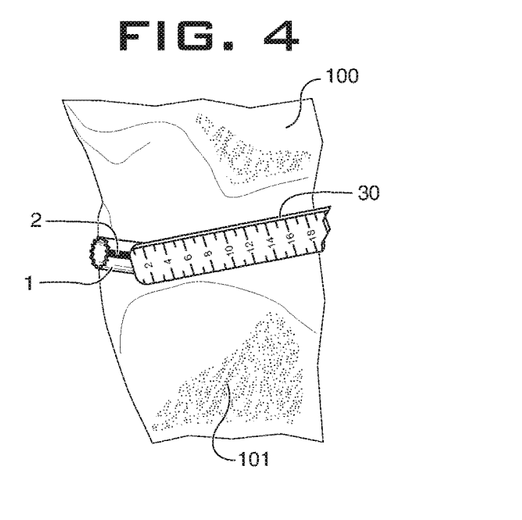
FIG. 4 is a perspective view of measurement of a desired distance from the first tunnel to a location for a second tunnel.
Figure 5:
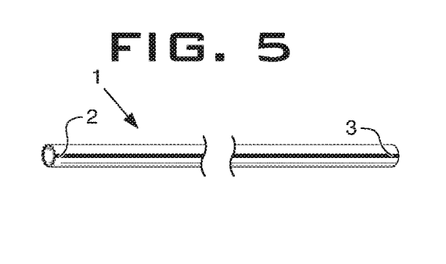
FIG. 5 is a side elevation view of a sleeved drill.

As illustrated in FIG. 4, method embodiments may include observing a radial position of the distal mark 2 on the sleeved drill 1 and orienting the sleeved drill 1 such that the distal mark 2 indicates a desired radial position to a second tunnel to be created through the tibia 100 such that an exit of the second tunnel is near a second portion of the soft tissue to be reattached. In particular in this embodiment, it may be desirable to select a second portion of the posterior root 201 to which a suture may be attached that may be used in combination with the attachment made to the first portion of the posterior root 201 to move the desired location of the medial meniscus 202 by coordinated tensioning of sutures attached to the posterior root 201. As depicted in FIG. 4, the distal mark 2 on the sleeved drill 1 has been oriented in a radial direction toward a second tunnel to be created in the tibia 100. This example further illustrates measuring a distance from the exit of the first tunnel to a desired location of the second tunnel. Specifically, a measuring instrument 30, as shown in FIG. 4, may be observed through an endoscope and oriented in the direction of the distal mark 2 to select a distance that is believed to be appropriate for a second tunnel through the tibia 100.

Some method embodiments also include observing a radial position of a proximal mark that correlates with an oriented distal mark. In the illustrated embodiment, this may include observing a radial position of the proximal mark 3 that correlates with the oriented position of the distal mark 2. Such an observation may provide a user with an orientation for creating the second tunnel relative to the first tunnel.

Figure 6:
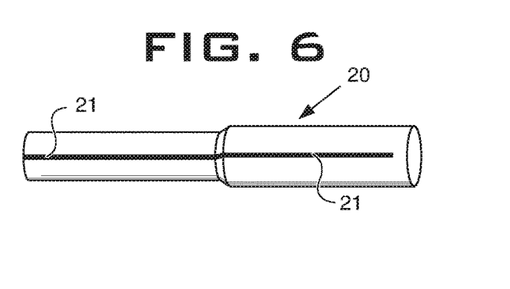
FIG. 6 is a side elevation view of an attachment for a sleeved drill.
Figures 7, 8:
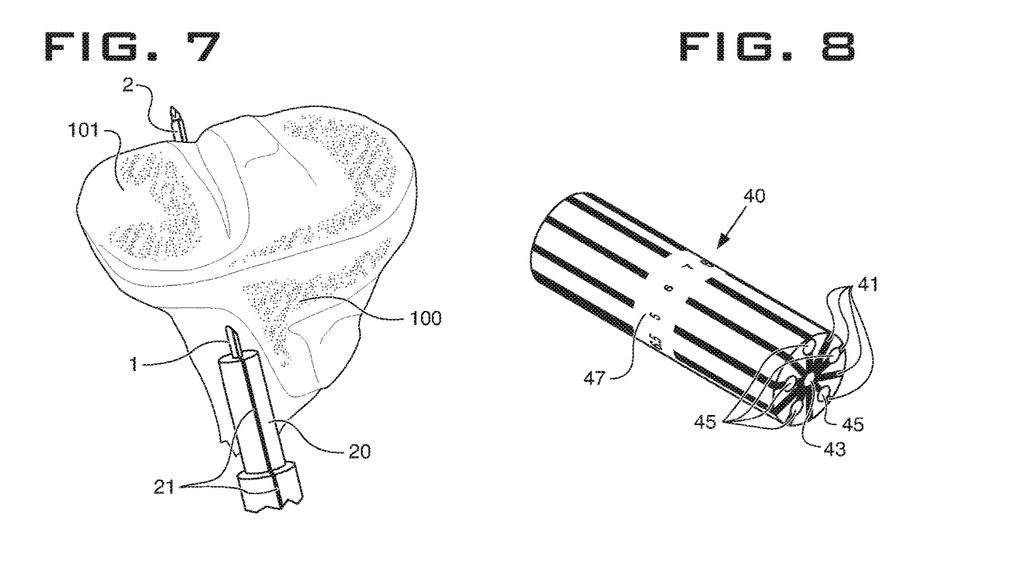
FIG. 7 is a perspective view of an attachment coupled with a sleeved drill that has been used to create a tunnel through a tibia.
FIG. 8 is a perspective view of a cylindrical drill guide.

An attachment 20 is illustrated in FIG. 6 and includes an attachment mark 21 to designate a radial position of the attachment 20. The attachment 20 is configured to couple with the proximal end of the sleeved drill 1 such that the attachment mark 21 aligns with the proximal mark 3 to further project the radial position of the proximal mark 3 to a user of the system. The attachment 20 is shown in FIG. 7 is projecting the attachment mark 21 in a radial position correlating with the oriented distal mark 2 and the proximal mark 3. The attachment 20 may be a handle, chuck, or other mechanism useful in manipulating the sleeved drill 1. An attachment of various embodiments may be configured to be manipulated or turned by hand or may provide for a coupling to an additional powered or non-powered manipulation device. The attachment 20 or a similar attachment may be used to turn the sleeved drill 1 to a desired radial position and may be manipulated or turned to affect drilling or other creation of a tunnel. After observing a radial position of the proximal mark 3 directly, or as projected by the attachment mark 21, a second tunnel may be created relative to the first tunnel at a radial direction from the first tunnel indicated by the proximal mark 3. In the illustrated embodiment, the position of the second tunnel relative to the first tunnel is a direct correlation. However, in other embodiments there may be one or both of a radial and a linear offset between a first tunnel and a second tunnel as measured by various instrument embodiments.

Figure 9:
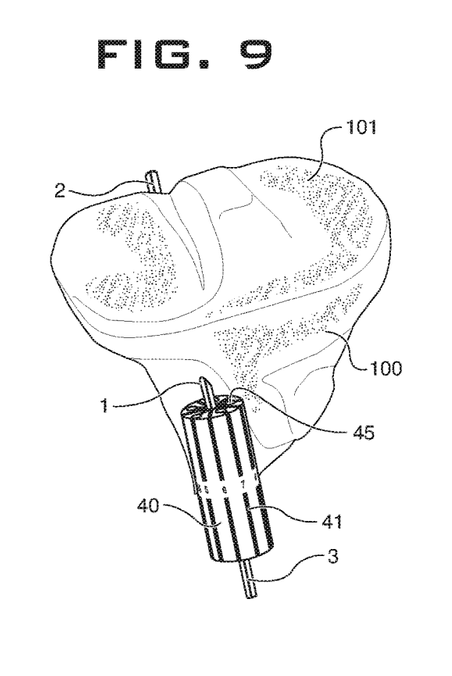
FIG. 9 is a perspective view of a cylindrical drill guide coupled with a sleeved drill that has been used to create a tunnel through a tibia.

Some method embodiments include the use of a drill guide, such as the drill guide 40 shown in FIGS. 8 and 9 that may be positioned relative to the first tunnel and used to guide the creation of the second tunnel. The drill guide 40 has multiple radial indicia 41 extending from a central hole 43 in the embodiment depicted. The drill guide 40 is a cylindrical drill guide and the central hole 43 is at the cross-sectional center of the cylinder and is configured to concentrically align with the first tunnel when the drill guide is positioned to be used to create the second tunnel. In other embodiments, a central hole or point about which a drill guide may engage an instrument that has been placed in a first tunnel may be in a geometric center of the drill guide or may be offset from a geometric center at some predetermined radial relationship. Such a drill guide may include indicia that designate relative radial positions. In still other embodiments, drilling of a second tunnel relative to a first tunnel may be accomplished with a set of drill guides or by use of any other method or instrument that allows for a second tunnel to be created relative to the first tunnel. The drill guide 40 shown is configured to fit over at least a portion of the sleeved drill 1. Any other effective mechanism for locating a drill guide relative to the sleeved drill 1 or another first instrument may be employed in other embodiments. The radial indicia 41 are configured to be aligned with the proximal mark 3 to provide a radial direction for the creation of the second tunnel, as illustrated in FIG. 9. The second tunnel of some embodiments is created substantially parallel with the first tunnel by use of a central hole 43 that is substantially parallel with a guide hole 45 through which creation of the second tunnel is accomplished. Each of the radial indicia 41 includes along its length a guide hole 45 at a predetermined distance from the central hole 43. In the embodiment illustrated, markings 47 label the predetermined distances between the central hole 43 and each of the respective guide holes 45 along respective radial indicia 41. As shown in FIG. 9, the proximal mark 3 is aligned with an indicium 41 on the drill guide 40 to radially align the position of a second tunnel to be created through a guide hole 45, which has a predetermined linear distance from the first tunnel in which the sleeved drill 1 has been placed of 7 mm. The selected the linear distance of 7 mm may have been selected by observation and use of the measuring instrument 30 illustrated in FIG. 4. In some embodiments, a final linear distance may be based on a measurement with a measuring instrument such as the measuring instrument 30 or by some other instrument that has been altered by an offset that accounts for the size of a sleeved drill, tunnel diameter, or some other known factor.

The second tunnel may be created with a second instrument such as a drill bit, which, for example, could be the drill bit 15 described herein. A drill bit may be used independently or in conjunction with another instrument to create a tunnel. For example, a drill bit may be used in combination with a sleeved drill such as the sleeved drill 1001 illustrated in FIGS. 10 and 11. The sleeved drill 1001 and the drill bit 15 may be used simultaneously by inserting the drill bit 15 inside of the sleeved drill 1001 during use or sequentially by first boring a hole with the drill bit 15 followed by passing the sleeved drill 1001 through the hole created by the drill bit 15. One or both of the sleeved drill 1001 and the drill bit 15 may be used through a guide hole, such as the guide hole 45, to create the second tunnel. Non-limiting examples of drill mechanisms in addition to bits include augers, stylets, corkscrews, or any other effective drilling mechanism. Any other instrument or combination of instruments that may be used to effectively create a tunnel through a bone may be used in various embodiments.

Figure 10:
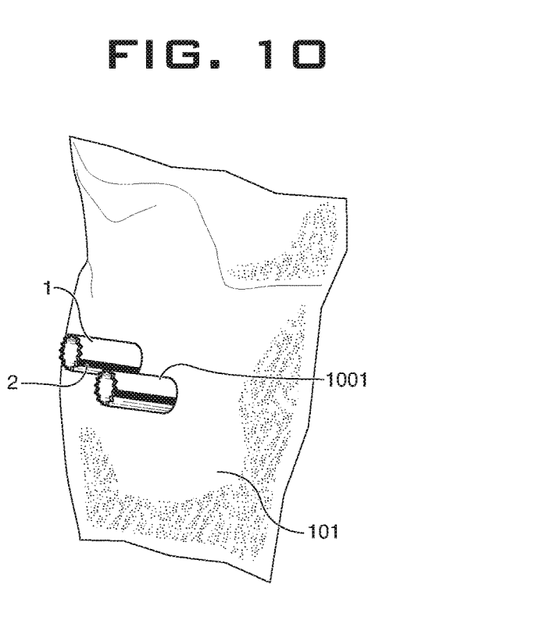
FIG. 10 is a perspective view of two substantially parallel sleeved drills that have been used to create or maintain two substantially parallel tunnels through a tibia.
Figure 11:
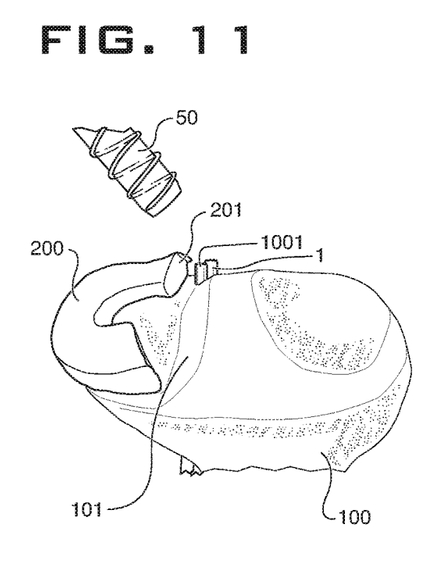
FIG. 11 is a perspective view of two substantially parallel sleeved drills that have been used to create tunnels through a tibia, with the tunnels exiting the tibia near a medial meniscus to be treated.

An example endoscopic portal 50 is illustrated in FIG. 11 through which acts of the methods disclosed herein may be accomplished or observed. Multiple endoscopic portals may be used to accomplish or observe acts of the methods disclosed herein. As illustrated in FIG. 10, the sleeved drill 1001 having been placed through the second tunnel aligned as disclosed herein is positioned in a radial direction consistent with the orientation of the distal mark 2.

Figure 12:
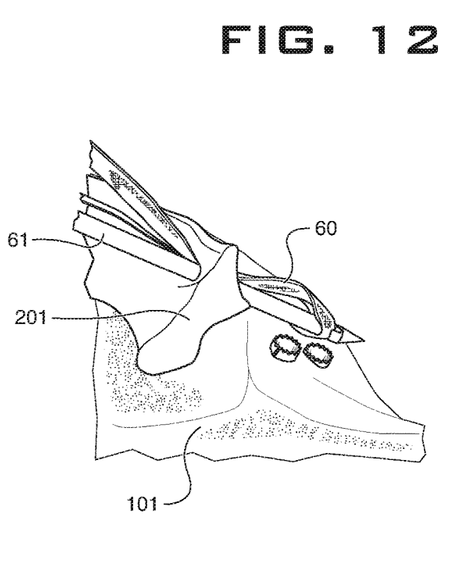
FIG. 12 is a perspective view of a tape type suture being passed through the medial meniscus to be treated.
Figure 13:
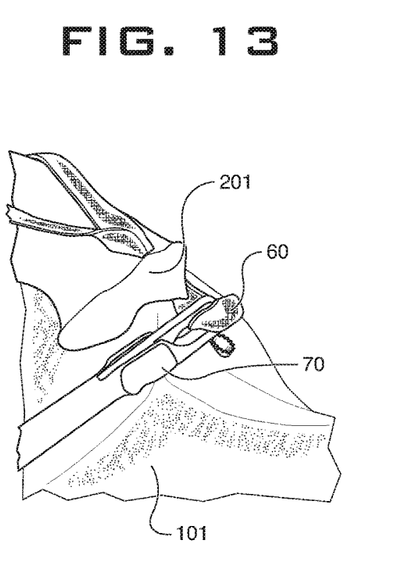
FIG. 13 is a perspective view of the tape type suture being further, selectively passed through the medial meniscus to be treated.
Figure 14:
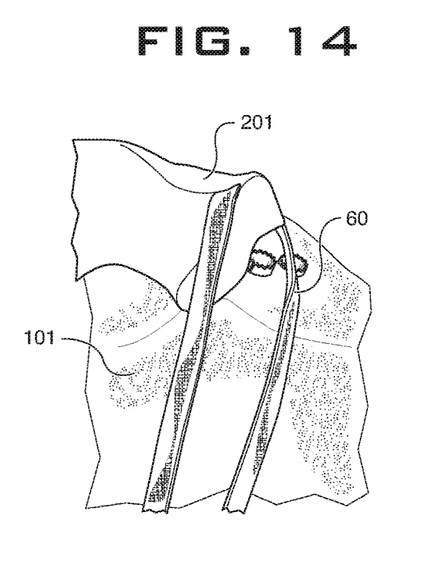
FIG. 14 is a perspective view of the tape type suture having been selectively passed through the medial meniscus to be treated.
Figure 15:
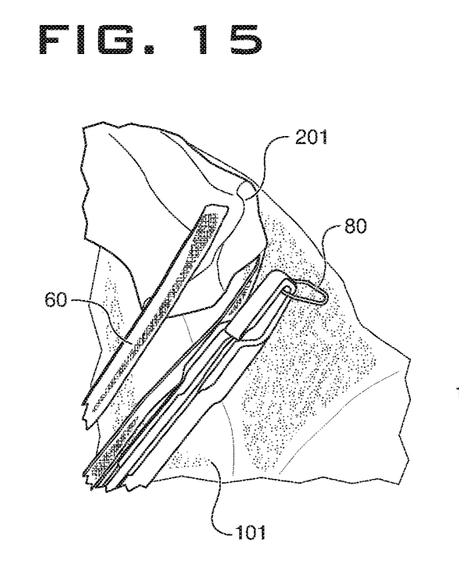
FIG. 15 is a perspective view of a looped guide wire being passed through a tunnel in the tibia.
Figure 16:
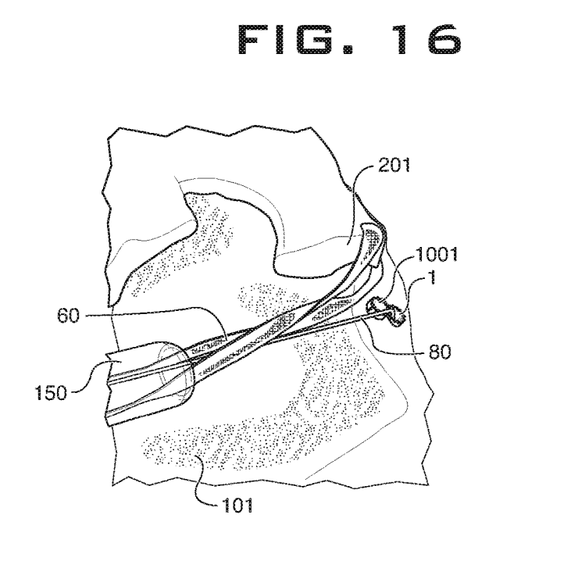
FIG. 16 is a perspective view of the looped guide wire and the tape type suture having been pulled into an endoscopic cannula to at least in part be coupled to one another.
Figures 17, 18:
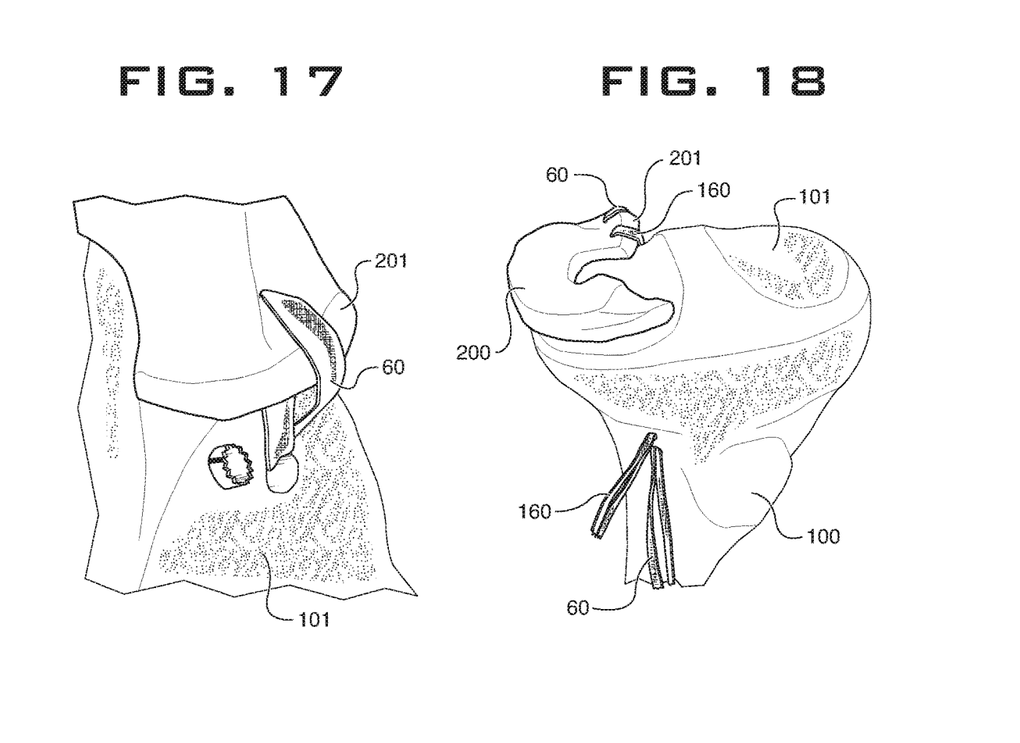
FIG. 17 is a perspective view of the tape type suture having been pulled through a first tunnel in the tibia.
FIG. 18 is a perspective view of another tape type suture having been pulled through a second tunnel in the tibia.
Figure 19:
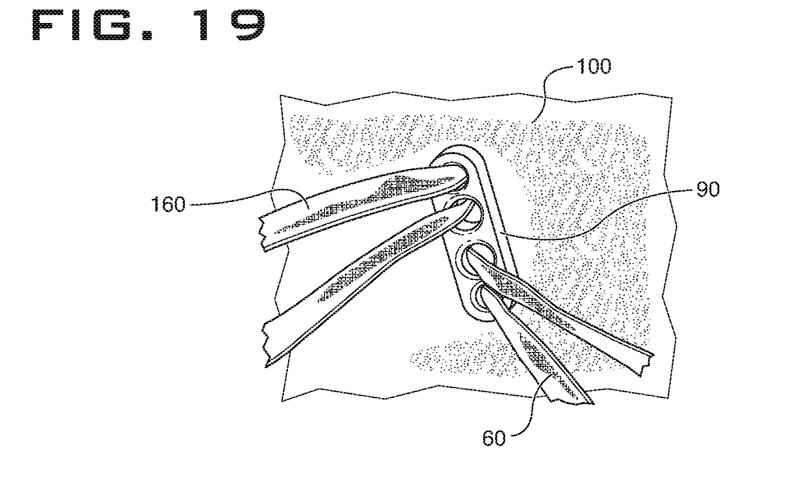
FIG. 19 is a perspective view of multiple tape type sutures positioned through an anchor.

As shown in FIG. 12, the sleeved drills 1, 1001 have been withdrawn to sit flush with the tibial plateau 101. A user may also choose to withdraw one or both of the sleeved drills 1, 1001 slightly sub-flush with the tibial plateau 101. A suture 60 that has been loaded onto a suture passer 61 is illustrated being coupled to the first portion of the posterior root 201 in FIG. 12. A looped grasper 70 is shown grasping a portion of the suture 60 in FIG. 13 to pull a leg of the suture 60 through the posterior root 201 to leave a simple stitch through the posterior root 201, as illustrated in FIG. 14. A looped guide wire 80 may then be introduced through one of the first or second tunnels as illustrated in FIG. 15. In the embodiment shown, the looped guide wire 80 has been introduced through the first tunnel. As shown in FIGS. 15 and 16, the looped guide wire 80 and the suture 60 may be retrieved through an endoscopic cannula 150. Method embodiments may further include withdrawing the sleeved drill 1 from the first tunnel and pulling the suture 60 through the first tunnel with the looped guide wire 80 to result in the structure illustrated in FIG. 17. In other embodiments, the first suture 60 may be passed through the second tunnel or another tunnel through the tibia. Some embodiments may also include passing one leg of the suture through one tunnel and another leg of the suture through another tunnel. Any other effective method of coupling a suture to soft tissue and passing the suture through the first tunnel may be employed in other embodiments of the invention. In a similar way a second suture 160 may be coupled to the second portion of the posterior root 201 and passed through at least one of the first tunnel and the second tunnel. The second suture 160 is shown coupled to the posterior root 201 and extending from the second tunnel in FIG. 18. The sutures 60, 160 illustrated are ULTRATAPE-brand tape type sutures that include multiple strands woven into an advantageous structure. ULTRATAPE is a trademark of Smith & Nephew, Inc., 1450 Brooks Road, Memphis, Tenn. However, other embodiments may be any effective known or later developed suture or similar structure capable of attaching between soft tissue and bone.

Figure 20:
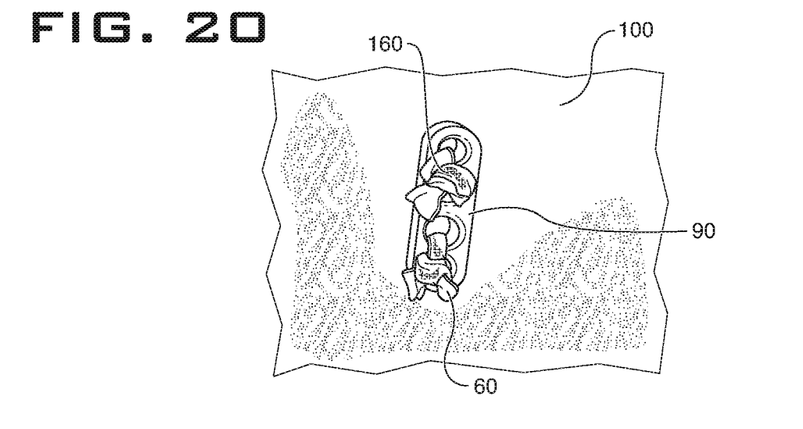
FIG. 20 is a perspective view of multiple tape type sutures secured to the anchor of FIG. 19.

A further act of some embodiments includes tensioning the first suture 60 to bring the first portion of the posterior root 201 into contact with the tibial plateau 101. The act of tensioning the first suture 60 may include moving the soft tissue to a desired location by tensioning. In other words, increasing tension in the first suture 60 may draw the first portion of the posterior root 201 toward the first tunnel, and decreasing tension in the first suture 60 may allow for tension from another suture such as the second suture 160 to move the posterior root 201 away from the first tunnel. When a desired tension for the first suture 60 is achieved, the first suture 60 may be secured relative to the tibia 100. As illustrated in FIGS. 18-21, the first suture 60 is passed through an anchor 90 near the entry point of the first bone tunnel into the tibia 100. The first suture 60 is secured to the anchor 90 to the desired tension by tying a knot next to the anchor 90, as illustrated in FIG. 20. The anchor 90 is an ENDOBUTTON-brand fixation device. ENDOBUTTON is a registered trademark of Smith & Nephew, Inc., 1450 Brooks Road, Memphis, Tenn. However, other embodiments may include use of any effective anchor or similar device, such as but not limited to, a washer, another type of proprietary suture anchor, an interference screw, a post, a tenodesis screw, or a knotless anchor.

A further act of some embodiments includes tensioning the second suture 160 to bring the second portion of the posterior root 201 into contact with the tibial plateau 101. The act of tensioning the second suture may include moving the soft tissue to a desired location by tensioning. In other words, increasing tension in the second suture 160 may draw the second portion of the posterior root 201 toward the second tunnel, and decreasing tension in the second suture 160 may allow for tension from another suture such as the first suture 60 to move the posterior root 201 away from the second tunnel. When a desired tension for the second suture 160 is achieved, the second suture 160 may be secured relative to the tibia 100. As illustrated in FIGS. 18-21, the second suture 160 is passed through the anchor 90 near the entry point of the second bone tunnel into the tibia 100. The second suture 160 is secured to the anchor 90 to the desired tension by tying a knot next to the anchor 90, as illustrated in FIG. 20. In the illustrated embodiment, the second suture 160 is secured to the same anchor 90 as the first suture 60. In other embodiments, various sutures may be secured to separate anchors, or more generally may be secured independently or interdependently.

Independent securing of the first suture 60 and the second suture 160 is valuable at least in circumstances where one of the sutures or its respective connection fails. With the disclosed embodiment, failure of one of the first suture 60 or the second suture 160 would not affect the other suture. Consequently, the posterior root 201 could at least in part be held in place relative to the tibial plateau 101 if a failure of one of the first suture 60 or the second suture 160 occurred. In some circumstances, this configuration could be important in avoiding an additional surgery to reattach the posterior root 201. Similarly, independence of the connections of the first suture 60 and the second suture 160 may be valuable in more effectively positioning the posterior root 201, as described in association with act related to tensioning of sutures herein.

Figure 21:
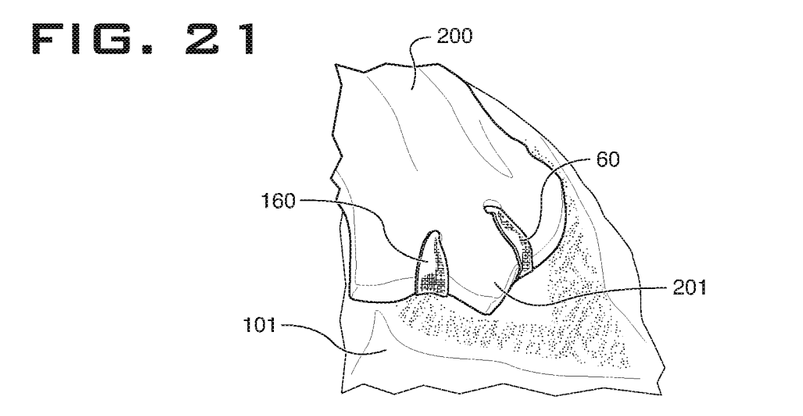
FIG. 21 is a perspective view of soft tissue reattached to bone with two tape type sutures.
Figure 22:
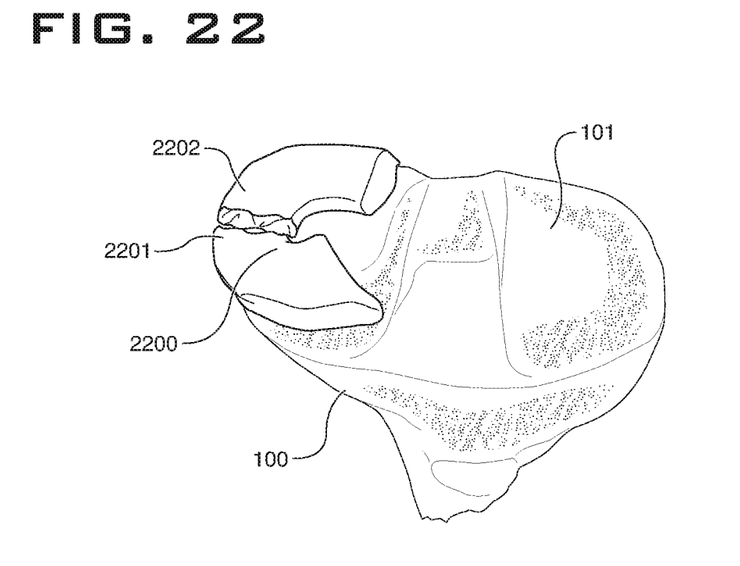
FIG. 22 is a perspective view of a tibial plateau and a portion of a medial meniscus with a radial tear.

A completed reattachment of soft tissue to bone is illustrated in FIG. 21. In particular, the posterior root 201 of the medial meniscus 200 is shown reattached to the tibial plateau 101 with the first suture 60 and the second suture 160.

Another method embodiment that includes creating a first tunnel through a bone, such as a tibia, such that an exit of the first tunnel is near a first portion of soft tissue to be reattached is illustrated in FIGS. 22-25. An aimer similar to the aimer 10 (FIG. 2) may be used to point to an exit through the tibial plateau 101 near a first portion of soft tissue 2201 (FIG. 22-25) of the medial meniscus 2200 to be reattached. An aimer and other instruments and implants of the methods disclosed herein may be used in combination with endoscopic visualization and manipulation tools. A drill bit may be used independently or in conjunction with another instrument to create a tunnel. For example, a drill bit may be used in combination with a sleeved drill such as the sleeved drill 2001 illustrated in FIG. 23. By way of further example, the sleeved drill 2001 and a drill bit may be used simultaneously by inserting the drill bit inside of the sleeved drill 2001 during use or sequentially by first boring a hole with the drill bit followed by passing the sleeved drill 2001 through the hole created by the drill bit. Non-limiting examples of drill mechanisms in addition to bits include augers, stylets, corkscrews, or any other effective drilling mechanism. Any other instrument or combination of instruments that may be used to effectively create a tunnel through a bone may be used in various embodiments. The sleeved drill 2001 is a tubular shaft that includes teeth and a distal mark 2002 near its distal end that designates a radial position of the sleeved drill 2001 by providing a line longitudinally along the sleeved drill 2001 at a radial position. The sleeved drill 2001 also includes a proximal mark 2003 near its proximal end that correlates with the radial position of the distal mark 2002. In this example, the proximal mark 2003 is also a line marked longitudinally along the sleeved drill 1 at a radial position. In the illustrated embodiment, the distal mark 2002 and the proximal mark 2003 are part of the same line marked longitudinally along the sleeved drill 2001; however, in other embodiments a distal mark and a proximal mark may have some correlation that does not necessarily include coexisting along the same line.

Figure 23:
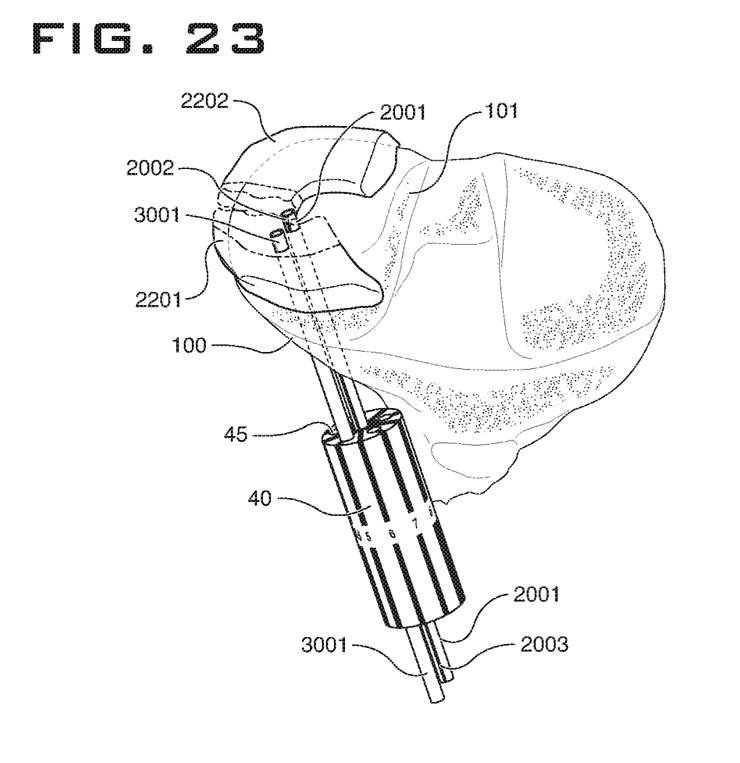
FIG. 23 is a perspective view of the tibial plateau and medial meniscus (which is in part illustrated as transparent) of FIG. 22 with a cylindrical drill guide coupled with two substantially parallel sleeved drills that have been used to create tunnels through the tibia.
Figure 24:
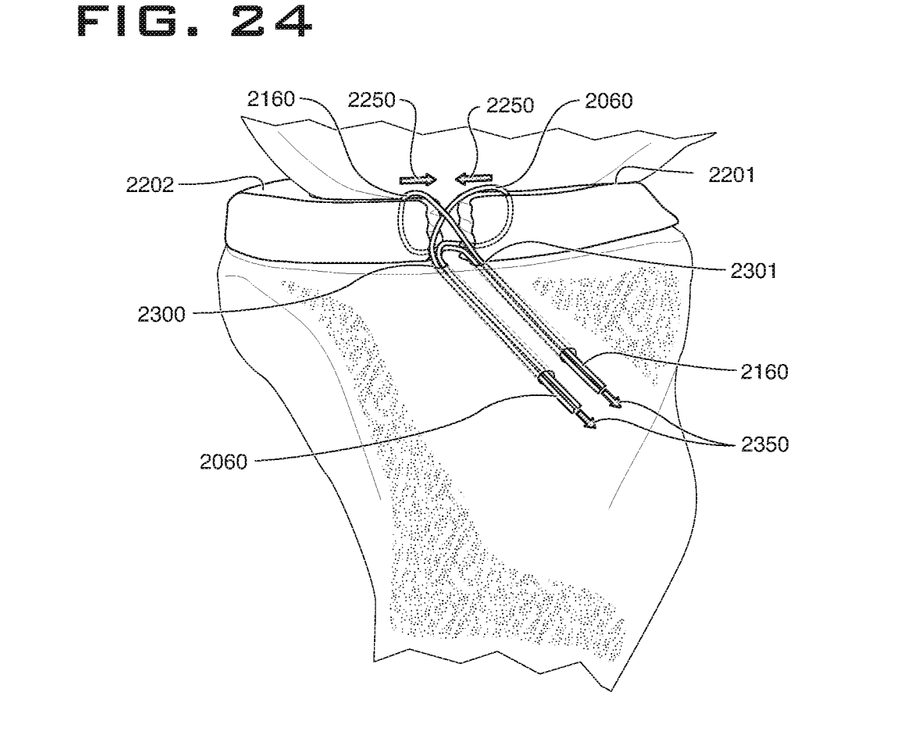
FIG. 24 is an elevation view of a medial meniscus with a radial tear that has been coupled with two sutures such that tension applied to the sutures, as illustrated with arrows showing tensile forces, will result in portions of the medial meniscus being drawn at least in part toward one another, as illustrated by the converging arrows.

As illustrated in FIG. 23, method embodiments may include observing a radial position of the distal mark 2002 on the sleeved drill 2001 and orienting the sleeved drill 2001 such that the distal mark 2002 indicates a desired radial position to a second tunnel to be created through the tibia 100 such that an exit of the second tunnel is near a second portion of the soft tissue to be reattached. In particular in this embodiment, it may be desirable to select a first portion of soft tissue 2201 of the medial meniscus 2200 and a second portion of soft tissue 2202 of the medial meniscus 2200 to which sutures may be attached that may be used to move the desired location of the medial meniscus 2200 or its parts by coordinated tensioning of sutures attached to the first and second portions of soft material 2201, 2202. As illustrated in FIG. 24, a first suture 2060 is coupled to first portion of soft tissue 2201 of the medial meniscus 2200 and is a first distance and first direction away from the exit 2300 of the first tunnel from the bone. A second suture 2160 is a second distance and second direction away from the exit 2301 of the second tunnel from the bone. In the illustrated embodiment, the first direction and the second direction are substantially opposite directions such that when one or both of the first suture 2060 and the second suture 2160 are tensioned, the first portion of soft tissue 2201 and the second portion of soft tissue 2202 are drawn at least in part toward one another. This relationship is further illustrated in FIG. 24 by arrows 2350 depicting tension applied to the first and second sutures 2060, 2160 resulting in drawing together of the first and second portions of soft tissue 2201, 2202 (converging arrows 2250). As used herein the term opposite directions does not mean only precisely opposite, but may also include generally opposing directions such that sutures extending from the respective tunnels that cross to attached tissue when tensioned would result in at least some opposing vector of force or movement for the tissue attached.

As depicted in FIG. 23, the distal mark 2002 on the sleeved drill 2001 has been oriented in a radial direction toward a second tunnel to be created in the tibia 100. A distance may be measured from the exit 2300 of the first tunnel to a desired location of the second tunnel. In this embodiment, measurement would be accomplished perpendicularly from a longitudinal axis of the first tunnel. A measuring instrument 30, as shown in FIG. 4, may be observed through an endoscope and oriented in the direction of the distal mark 2002 to select a distance that is believed to be appropriate for a second tunnel through the tibia 100.

Some method embodiments also include observing a radial position of a proximal mark that correlates with an oriented distal mark. In the illustrated embodiment, this may include observing a radial position of the proximal mark 2003 that correlates with the oriented position of the distal mark 2002. Such an observation may provide a user with an orientation for creating the second tunnel relative to the first tunnel.

An attachment such as the attachment 20 illustrated in FIG. 6 may be used with the sleeved drill 2001 substantially as described in association with FIG. 6. In the illustrated embodiment, the position of the second tunnel relative to the first tunnel is a direct correlation. However, in other embodiments there may be one or both of a radial and a linear offset between a first tunnel and a second tunnel as measured by various instrument embodiments.

Some method embodiments include the use of a drill guide such as the drill guide 40 shown in FIGS. 8, 9, and 23 that may be positioned relative to the first tunnel and used to guide the creation of the second tunnel. Use of the drill guide 40 with the embodiment illustrated in FIG. 23 is substantially the same as the use described in association with FIGS. 8 and 9.

The second tunnel may be created with a second instrument such as a drill bit, which, for example, could be the drill bit 15 described herein. A drill bit may be used independently or in conjunction with another instrument to create a tunnel. For example, a drill bit may be used in combination with a sleeved drill such as a sleeved drill 3001 illustrated in FIG. 23. The sleeved drill 3001 and a drill bit may be used simultaneously by inserting the drill bit inside of the sleeved drill 3001 during use or sequentially by first boring a hole with the drill bit followed by passing the sleeved drill 3001 through the hole created by the drill bit. One or both of the sleeved drill 3001 and a drill bit may be used through a guide hole, such as the guide hole 45, to create the second tunnel. Non-limiting examples of drill mechanisms in addition to bits include augers, stylets, corkscrews, or any other effective drilling mechanism. Any other instrument or combination of instruments that may be used to effectively create a tunnel through a bone may be used in various embodiments.

Figure 25:
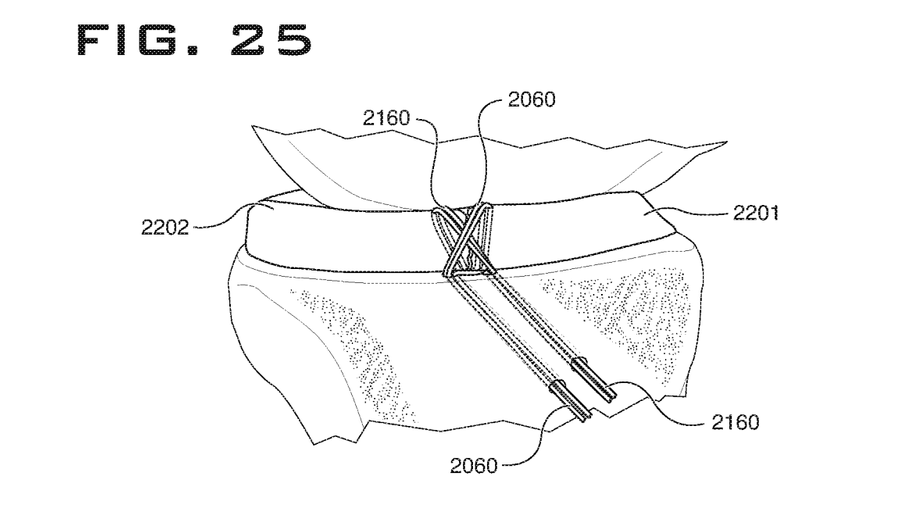
FIG. 25 is an elevation view illustrating a completed repair of a radial tear in a medial meniscus using two sutures in each of two portion of the medial meniscus being repaired.

First and second sutures 2060, 2160 may be passed through tunnels as illustrated in FIGS. 24 and 25 by any effective method, including the methods and variations of the methods described herein in association with FIGS. 12-20. The sutures 2060, 2160 illustrated are conventional sutures, but other suture embodiments may include any effective known or later developed suture or similar structure capable of attaching between soft tissue and bone. Example sutures include but not limited to ULTRATAPE-brand tape type sutures that have multiple strands woven into an advantageous structure. The completed reattachment shown in FIG. 25 includes two sutures in each of two portion of the medial meniscus being repaired. Other embodiments may include any effective number of sutures, may include sutures of different numbers, or may exhibit a complete omission of sutures in each of the first and second portions of soft tissue 2201, 2202. In some embodiments, portions of soft tissue may be suture directly together with suture that may or may not be connected through one or more tunnels through the bone. Such connections of portions of soft tissue together may also be accomplished with the use of staples, clips, or any effective mechanism or technique.

In addition to the acts of tensioning described in association with FIG. 24 above, some embodiments include tensioning the first suture 2060 to bring the first portion of soft tissue 2201 into contact with the tibial plateau 101. The act of tensioning the first suture 2060 may include moving the soft tissue to a desired location by tensioning. In other words, increasing tension in the first suture 2060 may draw the first portion of soft tissue 2201 toward the first tunnel, and decreasing tension in the first suture 2060 may allow for tension from another suture to move the first portion of soft tissue 2201 away from the first tunnel. When a desired tension for the first suture 2060 is achieved, the first suture 2060 may be secured relative to the tibia 100. Any effective anchor or similar device, such as but not limited to, a washer, another type of proprietary suture anchor, an interference screw, a post, a tenodesis screw, or a knotless anchor may be used to secure the first suture 2060 relative to the tibia 100. Some embodiments include tensioning the second suture 2160 to bring the second portion of soft tissue 2202 into contact with the tibial plateau 101. The act of tensioning the second suture 2160 may include moving the soft tissue to a desired location by tensioning. In other words, increasing tension in the second suture 2160 may draw the second portion of soft tissue 2202 toward the second tunnel, and decreasing tension in the second suture 2160 may allow for tension from another suture to move the second portion of soft tissue 2202 away from the second tunnel. When a desired tension for the second suture 2160 is achieved, the second suture 2160 may be secured relative to the tibia 100. Any effective anchor or similar device, such as but not limited to, a washer, another type of proprietary suture anchor, an interference screw, a post, a tenodesis screw, or a knotless anchor may be used to secure the second suture 2160 relative to the tibia 100. Various sutures may be secured to separate anchors, or more generally may be secured independently or interdependently.

Independent securing of the first suture 2060 and the second suture 2160 is valuable at least in circumstances where one of the sutures or its respective connection fails. With the disclosed embodiment, failure of one of the first suture 2060 or the second suture 2160 would not affect the other suture, and would have a limited effect on the entire construct if the first and second portions of soft tissue 2201, 2202 also are sutured together. The medial meniscus 2200 could at least in part be held in place relative to the tibial plateau 101 if a failure of one of the first suture 2060 or the second suture 2160 occurred. In some circumstances, this configuration could be important in avoiding an additional surgery to reattach the medial meniscus 2200. Similarly, independence of the connections of the first suture 2060 and the second suture 2160 may be valuable in more effectively positioning the medial meniscus 2200, as described in association with act related to tensioning of sutures herein.

A completed reattachment of soft tissue to bone is illustrated in FIG. 25. In particular, the medial meniscus 2200 is shown reattached to the tibial plateau 101 with the first suture 2060, the second suture 2160, and additional sutures.

An embodiment of the present invention describes a method of placing two substantially parallel tunnels in a bone with a controlled distance and relative radial position between the two tunnels. Such an embodiment is depicted in two circumstances: in FIGS. 2-7; and in FIG. 23. As one example illustrated in FIGS. 2-7, and as described in more detail herein, a first tunnel may be created in the tibia 100. Such method embodiments may further include placing a first instrument, such as the sleeved drill 1, through the first tunnel. The sleeved drill 1 includes the distal mark 2 near its end to designate a radial position of the sleeved drill 1. The sleeved drill one also includes the proximal mark 3 near its proximal end that correlates with the distal mark 2.

Method embodiments may include observing a radial position of the distal mark 2 on the sleeved drill 1 and orienting the sleeved drill 1 such that the distal mark 2 indicates a desired radial position to a second tunnel to be created through the tibia 100. As depicted in FIG. 4, the distal mark 2 on the sleeved drill 1 has been oriented in a radial direction toward a second tunnel to be created in the tibia 100. This example further illustrates measuring a distance from the exit of the first tunnel to a desired location of the second tunnel. Specifically, a measuring instrument 30, as shown in FIG. 4, may be observed through an endoscope and oriented in the direction of the distal mark 2 to select a distance that is believed to be appropriate for a second tunnel through the tibia 100.

Some method embodiments also include observing a radial position of a proximal mark that correlates with an oriented distal mark. In the illustrated embodiment, this may include observing a radial position of the proximal mark 3 that correlates with the oriented position of the distal mark 2. Such an observation may provide a user with an orientation for creating the second tunnel relative to the first tunnel.

An attachment 20 is illustrated in FIG. 6 and includes an attachment mark 21 to designate a radial position of the attachment 20. The attachment 20 is configured to couple with the proximal end of the sleeved drill 1 such that the attachment mark 21 aligns with the proximal mark 3 to further project the radial position of the proximal mark 3 to a user of the system. The attachment 20, as shown in FIG. 7, is projecting the attachment mark 21 in a radial position correlating with the oriented distal mark 2 and the proximal mark 3. The attachment 20 may be a handle, chuck, or other mechanism useful in manipulating the sleeved drill 1. An attachment of various embodiments may be configured to be manipulated or turned by hand or may provide for a coupling to an additional powered or non-powered manipulation device. The attachment 20 or a similar attachment may be used to turn the sleeved drill 1 to a desired radial position and may be manipulated or turned to affect drilling or other creation of a tunnel. After observing a radial position of the proximal mark 3 directly, or as projected by the attachment mark 21, a second tunnel may be created relative to the first tunnel at a radial direction from the first tunnel indicated by the proximal mark 3. In the illustrated embodiment, the position of the second tunnel relative to the first tunnel is a direct correlation. However, in other embodiments there may be one or both of a radial and a linear offset between a first tunnel and a second tunnel as measured by various instrument embodiments.

Some method embodiments related to placing two substantially parallel tunnels in a bone with a controlled distance and relative radial position between the two tunnels include the use of a drill guide, such as the drill guide 40 shown in FIGS. 8 and 9 and described in detail herein, that may be positioned relative to the first tunnel and used to guide the creation of the second tunnel. The second tunnel may be created substantially parallel with the first tunnel by use of a central hole 43 that is substantially parallel with a guide hole, such as one of the guide holes 45, through which creation of the second tunnel is accomplished. Any other effective mechanism to fix a guide relative to the first tunnel and provide a substantially parallel pathway to a second tunnel that is substantially parallel to the first tunnel may be used in various embodiments.

Other characteristics and uses of the drill guide 40 used for placing two substantially parallel tunnels in a bone with a controlled distance and relative radial position between the two tunnels are essentially similar to the characteristics and uses of the drill guide 40 described in detail herein. The second tunnel may be created with a second instrument such as a drill bit used independently or in conjunction with another instrument to create a tunnel. Non-limiting examples of other drill tunnel creation mechanisms that may be used in some embodiments include augers, stylets, corkscrews, or any other effective mechanism.

Further, there is provided a method of reattaching soft tissue to a bone, such as a tibia. As examples, the soft tissue may be meniscal tissue near a medial posterior root or torn radial meniscal tissue. The method includes: creating a first tunnel through the bone such that an exit of the first tunnel is near a first portion of the soft tissue to be reattached; placing a first instrument through the first tunnel, wherein the first instrument includes a distal mark near its distal end to designate a radial position of the first instrument and a proximal mark near its proximal end that correlates with the distal mark; observing a radial position of the distal mark on the first instrument and orienting the first instrument such that the distal mark indicates a desired radial position to a second tunnel to be created through the bone such that an exit of the second tunnel is near a second portion of the soft tissue to be reattached; observing a radial position of the proximal mark that correlates with the oriented distal mark; creating the second tunnel relative to the first tunnel at a radial direction from the first tunnel indicated by the proximal mark; coupling a first suture to the first portion of the soft tissue to be reattached and passing the first suture through at least one of the first tunnel and the second tunnel; coupling a second suture to the second portion of the soft tissue to be reattached and passing the second suture through at least one of the first tunnel and the second tunnel; tensioning the first suture to bring the soft tissue into contact with the bone; securing the first suture relative to the bone; tensioning the second suture to bring the soft tissue into contact with the bone; and securing the second suture relative to the bone.

The method may include the act of placing a first instrument through the first tunnel includes creating the first tunnel through the bone.

The method may include the act of observing a radial position of the distal mark includes observation through an endoscope.

The method may include the act of measuring a distance from the exit of the first tunnel to a desired location of the second tunnel.

The method may include a drill guide positioned relative to the first tunnel and used to guide the creation of the second tunnel. Further, the method may include aligning the proximal mark with an indicia on the drill guide to radially align the position of the second tunnel relative to the first tunnel. Also, the method may include aligning the proximal mark with a cylindrical drill guide having a central hole that is configured to concentrically align with the first tunnel and includes two or more guide holes at different radial directions and different distances form the central hole. Further, the method may include fitting the central hole over at least a portion of the first instrument.

The method may include the act of placing a second instrument through the second tunnel. Further, the method may include the act of placing a second instrument through the second tunnel and includes creating the second tunnel through the bone.

The method may include the act of passing the first suture and the second suture through at least one of the first tunnel and the second tunnel includes passing the first suture through the first tunnel and the second suture through the second tunnel.

The method may include the act of coupling the first suture and includes coupling a suture that is a tape type suture. Additionally, the method may include the act of coupling the second suture and includes coupling a suture that is a tape type suture.

The method may include the act of tensioning the first suture and includes moving the soft tissue to a desired location by the tensioning.

The method may include the act of securing the first suture relative to bone and includes securing the first suture near a bone tunnel entry point.

The method may include the act of securing the first suture relative to bone and includes securing the first suture to an anchor.

The method may include the act of tensioning the second suture and includes moving the soft tissue to a desired location by the tensioning.

The method may include the act of securing the second suture relative to bone and includes securing the second suture near a bone tunnel entry point.

The method may include the act of securing the second suture relative to the bone and includes securing the second suture to an anchor.

The method may include the act of securing the second suture relative to the bone and includes securing the second suture to an anchor to which the first suture is or will be secured.

The method may include the act of coupling the first portion of the soft tissue to be reattached to the second portion of the soft tissue to be reattached.

The method may include the act of coupling the first suture to a first portion of soft tissue and includes coupling the first suture to a first portion of soft tissue that is a first distance and first direction away from the exit of the first tunnel from the bone, wherein the act of coupling the second suture to a second portion of soft tissue includes coupling the second suture to a second portion of soft tissue that is a second distance and second direction away from the exit of the second tunnel from the bone, and wherein the first direction and the second direction are substantially opposite directions; such that when one or both of the first suture and the second suture are tensioned, the first portion of soft tissue and the second portion of soft tissue are drawn at least in part toward one another.

There is also provided a method of placing two substantially parallel tunnels in a bone with a controlled distance and relative radial position between the two tunnels. The method includes: creating a first tunnel in the bone; placing a first instrument through the first tunnel, wherein the first instrument includes a distal mark near its distal end to designate a radial position of the first instrument and a proximal mark near its proximal end that correlates with the distal mark; observing a radial position of the distal mark on the first instrument and orienting the first instrument such that the distal mark indicates a desired radial position to a second tunnel to be created in the bone; measuring a distance from the exit of the first tunnel to a desired location of the second tunnel; observing a radial position of the proximal mark that correlates with the oriented distal mark; and creating the second tunnel relative to the first tunnel at a radial direction indicated by the proximal mark.

The method may include the act of placing a first instrument through the first tunnel and includes creating the first tunnel through the bone.

The method may include the act of observing a radial position of the distal mark and includes observation through an endoscope.

The method may include the act of positioning a drill guide relative to the first tunnel and used to guide the creation of the second tunnel. The method may include the act of aligning the proximal mark with an indicia on the drill guide to radially align the position of the second tunnel relative to the first tunnel. In one variation of the method, the proximal mark is aligned with a cylindrical drill guide having a central hole that is configured to concentrically align with the first tunnel and includes two or more guide holes at different radial directions and different distances form the central hole. The central hole may be configured to fit over at least a portion of the first instrument.

The method may include the act of placing a second instrument through the second tunnel. The method may include the act of placing a second instrument through the second tunnel and includes creating the second tunnel through the bone.

Further, there is provided an instrument set for creating two substantially parallel tunnels in a bone with a controlled distance and relative radial position between the two tunnels. The instrument set may include: a first instrument configured to create or maintain a first tunnel through the bone, the first instrument including: a shaft with a proximal end and a distal end, a distal mark near the distal end of the shaft configured to designate a radial position of the first instrument, and a proximal mark near the proximal end of the shaft that correlates with the radial position of the distal mark; a drill guide with two or more radial indicia extending from a central hole, the radial indicia being configured to be aligned with the proximal mark to provide a radial direction for the creation of a second tunnel that is substantially parallel with the first tunnel, wherein two or more of the radial indicia include along their respective lengths a respective guide hole at a predetermined distance from the central hole; and a second instrument configured to be passed through at least one of the guide holes to create a second tunnel that is substantially parallel with the first tunnel.

The instrument set may include the first instrument with a sleeved drill. Further, the instrument set may include the first instrument with an inner shaft configured to couple within the sleeved drill while the first instrument is deployed to create a tunnel.

The instrument set may include the drill guide with the central hole sized to be received over the first drill. The instrument set may include the drill guide and the drill guide is a cylindrical drill guide and the central hole is at the cross-sectional center of the cylinder and is configured to concentrically align with the first tunnel when the drill guide is in position to be used to create the second tunnel. Also, the instrument set may include the drill guide and the drill guide includes numerical values associated with respective radial indicia and displayed on the drill guide to indicate respective predetermined distances from the first tunnel to the second tunnel to be created.

The instrument set may include the second instrument with a sleeved drill. Further, the instrument set may include the second instrument with an inner shaft configured to couple within the sleeved drill while the second instrument is deployed to create a tunnel.

The instrument set may include an attachment that includes a radial mark that is configured to radially align with the proximal mark to provide a more easily recognizable display of a radial direction the proximal mark.

Various embodiments of a system wholly or its components individually may be made from any biocompatible material. For example and without limitation, biocompatible materials may include in whole or in part: non-reinforced polymers, reinforced polymers, metals, ceramics, adhesives, reinforced adhesives, and combinations of these materials. Reinforcing of polymers may be accomplished with carbon, metal, or glass or any other effective material. Examples of biocompatible polymer materials include polyamide base resins, polyethylene, Ultra High Molecular Weight (UHMW) polyethylene, low density polyethylene, polymethylmethacrylate (PMMA), polyetheretherketone (PEEK), poly etherketoneketone (PEKK), a polymeric hydroxyethylmethacrylate (PHEMA), and polyurethane, any of which may be reinforced. Polymers used as bearing surfaces in particular may in whole or in part include one or more of cross-linked and highly cross-linked polyethylene. Example biocompatible metals include stainless steel and other steel alloys, cobalt chrome alloys, zirconium, oxidized zirconium, tantalum, titanium, titanium alloys, titanium-nickel alloys such as Nitinol and other superelastic or shape-memory metal alloys.

Terms such as proximal, distal, medial, posterior, near, over, next to, inside, and the like have been used relatively herein. However, such terms are not limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A kit comprising one or more lengths of suture and an instrument set for creating two substantially parallel tunnels in a bone with a controlled distance and relative radial position between the two tunnels, wherein the two substantially parallel tunnels are sized and configured to receive the one or more lengths of suture, the instrument set comprising:
   a first instrument configured to create and maintain a first tunnel through the bone while suture is advanced through the first tunnel, the first instrument comprising:
      a tubular shaft with a proximal end and a distal end,
      a distal mark near the distal end of the shaft configured to designate a radial position of the first instrument, and
      a proximal mark near the proximal end of the shaft that correlates with the radial position of the distal mark;
   a drill guide with two or more radial indicia extending from a central hole, the radial indicia being configured to be aligned with the proximal mark to provide a radial direction for the creation of a second tunnel that is substantially parallel with the first tunnel, wherein two or more of the radial indicia include along their respective lengths a respective guide hole at a predetermined distance from the central hole; and
   a second instrument configured to be passed through at least one of the guide holes to create and maintain a second tunnel through the bone while suture is advanced through the second tunnel, wherein the second tunnel is substantially parallel with the first tunnel.

2. The kit of claim 1 wherein the first instrument includes an inner shaft configured to couple within the tubular shaft while the first instrument is deployed to create a tunnel.

3. The kit of claim 1 wherein the central hole of the drill guide is sized to be received over the tubular shaft.

4. The kit of claim 1 wherein the drill guide is a cylindrical drill guide and the central hole is at a cross-sectional center of the cylinder and is configured to concentrically align with the first tunnel when the drill guide is in position to be used to create the second tunnel.

5. The kit of claim 1 wherein the drill guide includes numerical values associated with respective radial indicia and displayed on the drill guide to indicate respective predetermined distances from the first tunnel to the second tunnel to be created.

6. The kit of claim 1 wherein the second instrument includes a sleeved drill.

7. The kit of claim 6 wherein the second instrument includes an inner shaft configured to couple within the sleeved drill while the second instrument is deployed to create a tunnel.

8. The kit of claim 1, further comprising an attachment that includes a radial mark that is configured to radially align with the proximal mark to provide a more easily recognizable display of a radial direction the proximal mark.

9. An instrument set for creating two substantially parallel tunnels in a bone with a controlled distance and relative radial position between the two tunnels comprising:
   a first instrument configured to create and maintain a first tunnel through the bone comprising:
      a tubular shaft with a proximal end and a distal end,
      a distal mark near the distal end of the shaft configured to designate a radial position of the first instrument, and
      a proximal mark near the proximal end of the shaft that correlates with the radial position of the distal mark;
   a drill guide with two or more radial indicia extending from a central hole, the radial indicia being configured to be aligned with the proximal mark to provide a radial direction for the creation of a second tunnel that is substantially parallel with the first tunnel, wherein two or more of the radial indicia include along their respective lengths a respective guide hole at a predetermined distance from the central hole; and
   a second instrument configured to be passed through at least one of the guide holes to create and maintain a second tunnel that is substantially parallel with the first tunnel.

10. The instrument set of claim 9 wherein the first instrument includes an inner shaft configured to couple within the tubular shaft while the first instrument is deployed to create a tunnel.

11. The instrument set of claim 9 wherein the central hole of the drill guide is sized to be received over the tubular shaft.

12. The instrument of claim 9 wherein the drill guide is a cylindrical drill guide and the central hole is at a cross-sectional center of the cylinder and is configured to concentrically align with the first tunnel when the drill guide is in position to be used to create the second tunnel.

13. The instrument set of claim 9 wherein the drill guide includes numerical values associated with respective radial indicia and displayed on the drill guide to indicate respective predetermined distances from the first tunnel to the second tunnel to be created.

14. The instrument set of claim 9 wherein the second instrument includes a sleeved drill.

15. The instrument set of claim 14 wherein the second instrument includes an inner shaft configured to couple within the sleeved drill while the second instrument is deployed to create a tunnel.

16. The instrument set of claim 9, further comprising an attachment that includes a radial mark that is configured to radially align with the proximal mark to provide a more easily recognizable display of a radial direction the proximal mark.

* * * * *